(12) United States Patent
Persson et al.

(10) Patent No.: US 11,951,220 B2
(45) Date of Patent: Apr. 9, 2024

(54) STORAGE DEVICE FOR HEADPHONES

(71) Applicant: DEGAUSS LABS AB, Stockholm (SE)

(72) Inventors: Claes Persson, Stockholm (SE);
Nicolas Persson, Stockholm (SE)

(73) Assignee: DEGAUSS LABS AB, Stockholm (SE)

( * ) Notice: Subject to any disclaimer, the term of this patent is extended or adjusted under 35 U.S.C. 154(b) by 1041 days.

(21) Appl. No.: 16/753,768

(22) PCT Filed: Oct. 6, 2017

(86) PCT No.: PCT/SE2017/050979
§ 371 (c)(1),
(2) Date: Apr. 4, 2020

(87) PCT Pub. No.: WO2019/070175
PCT Pub. Date: Apr. 11, 2019

(65) Prior Publication Data
US 2020/0353110 A1 Nov. 12, 2020

(51) Int. Cl.
*A61L 2/10* (2006.01)
*A45C 11/00* (2006.01)
(Continued)

(52) U.S. Cl.
CPC ............ *A61L 2/10* (2013.01); *A45C 11/00* (2013.01); *A45C 15/00* (2013.01); *A61L 2/26* (2013.01); *B08B 7/005* (2013.01); *B08B 7/0057* (2013.01); *B08B 7/04* (2013.01); *H02J 7/0045* (2013.01); *H02J 7/02* (2013.01); *H04B 5/79* (2024.01); *H04R 1/1025* (2013.01); *H04R 1/12* (2013.01); *A45C 2011/001* (2013.01);
(Continued)

(58) Field of Classification Search
CPC .......... A61L 2/10; A61L 2/26; A61L 2202/11; A61L 2202/16; A61L 2202/17; A61L 2/081; A61L 2/082; A61L 2/085; A45C 11/00; A45C 15/00; A45C 2011/001; B08B 7/005; B08B 7/0057; B08B 7/04; B08B 7/0035; H02J 7/0045; H02J 7/02; H04B 5/0037; H04B 5/79; H04R 1/1025; H04R 1/12; H04R 2460/17; Y02T 10/70; Y02T 10/7072; Y02T 90/12; B60L 53/30; A47L 25/00
USPC .................................................... 250/455.11
See application file for complete search history.

(56) References Cited

U.S. PATENT DOCUMENTS

| 8,597,588 B1 | 12/2013 | Trabalka et al. |
| 2009/0080679 A1* | 3/2009 | Rass ............ H04R 1/12 381/322 |

(Continued)

FOREIGN PATENT DOCUMENTS

| CN | 201674643 U | 12/2010 |
| CN | 204395050 U | 6/2015 |

(Continued)

OTHER PUBLICATIONS

International Search Report from corresponding International Application No. PCT/SE2017/050979, dated Jun. 15, 2018, 3 pages.

*Primary Examiner* — Kiet T Nguyen
(74) *Attorney, Agent, or Firm* — Tucker Ellis LLP

(57) ABSTRACT

The present invention refers to a storage device for headphones comprising a compartment for non liquid means for cleaning the headphones and/or means for charging electronic devices. It further refers to a cleaning device for headphones.

5 Claims, 1 Drawing Sheet

(51) Int. Cl.
*A45C 15/00* (2006.01)
*A61L 2/26* (2006.01)
*B08B 7/00* (2006.01)
*B08B 7/04* (2006.01)
*H02J 7/00* (2006.01)
*H02J 7/02* (2016.01)
*H04B 5/79* (2024.01)
*H04R 1/10* (2006.01)
*H04R 1/12* (2006.01)

(52) U.S. Cl.
CPC ........ *A61L 2202/11* (2013.01); *A61L 2202/16* (2013.01); *A61L 2202/17* (2013.01); *H04R 2460/17* (2013.01)

(56) References Cited

U.S. PATENT DOCUMENTS

| | | | |
|---|---|---|---|
| 2009/0296968 A1* | 12/2009 | Wu | H04R 25/00 |
| | | | 381/323 |
| 2014/0044293 A1 | 2/2014 | Ganem et al. | |
| 2014/0056758 A1 | 2/2014 | Trabalka et al. | |
| 2015/0162770 A1* | 6/2015 | Choi | A61L 2/24 |
| | | | 34/88 |
| 2016/0158395 A1* | 6/2016 | Hughes | A61L 2/10 |
| | | | 250/455.11 |
| 2017/0319725 A1* | 11/2017 | Hann | A61L 2/10 |
| 2018/0324515 A1* | 11/2018 | Boesen | H04R 1/1041 |
| 2019/0297437 A1* | 9/2019 | Gil | F26B 9/003 |

FOREIGN PATENT DOCUMENTS

| | | |
|---|---|---|
| CN | 204561192 U | 8/2015 |
| CN | 206136206 U | 4/2017 |

* cited by examiner

STORAGE DEVICE FOR HEADPHONES

FIELD OF THE INVENTION

The present invention refers to a storage device for headphones, which device also comprises means for cleaning the headphones and means for charging the head phones.

BACKGROUND OF THE INVENTION

The use of different headphones, or earphones, with electronic devices has increased during the last years. More specifically, the use of wireless headphones has increased dramatically.

So called in-ear headphones, sometimes in combination with Bluetooth technique, are commonly used together with mobile phones and other electronic devices. In-ear headphones come into daily contact with for example ear wax, sweat and make-up. The headphones are not only dirty, they could also carry bacteria that could lead to infections if they come into contact with wounds.

Furthermore, any oils or ear wax left on the headphones can impact the sound quality of the headphones.

Cleaning of headphones has traditionally been done by wiping the them off with a dry or mildly wetted cloth, wipes, napkins or the like. It is not possible to soak them into a liquid to clean them since the electronics can be destroyed. It is however hard to get the in-ear headphones completely clean by only wiping them off.

One possible solution for cleaning is the use of electromagnetic radiation. The use of UV-light for sanitization has previously been used for example to clean toothbrushes, where the toothbrush is placed in a casing and the UV-light is turned on and the toothbrush cleaned inside the casing.

Other examples when UV-light is used for example in water treatment. These systems are however much more complicated than what is needed for the product described herein.

Hence, there is a problem that in-ear headphones are dirty and hard to clean.

SUMMARY OF THE INVENTION

The present invention solves this and other problems with a storage device comprising cleaning means as well as means for charging electronic devices.

The storage device according to the present invention comprises a compartment for non liquid means for cleaning the headphones and/or means for charging electronic devices.

The present invention also refers to a cleaning device for headphones.

BRIEF DESCRIPTION OF THE DRAWINGS

In the following, the invention will be described in detail, with reference to exemplifying embodiments of the invention and to the enclosed drawings, in which.

DETAILED DESCRIPTION OF THE INVENTION

The storage device according to the present invention is a casing, a housing or any other suitable device for storing headphones. The storage device will protect the head phones while not in use and when the head phones are placed inside the storage device and the lid is closed, the headphones can be charged, either by attaching a cable for charging or inductive charging by NFC or other similar charging technique.

Figure 1:
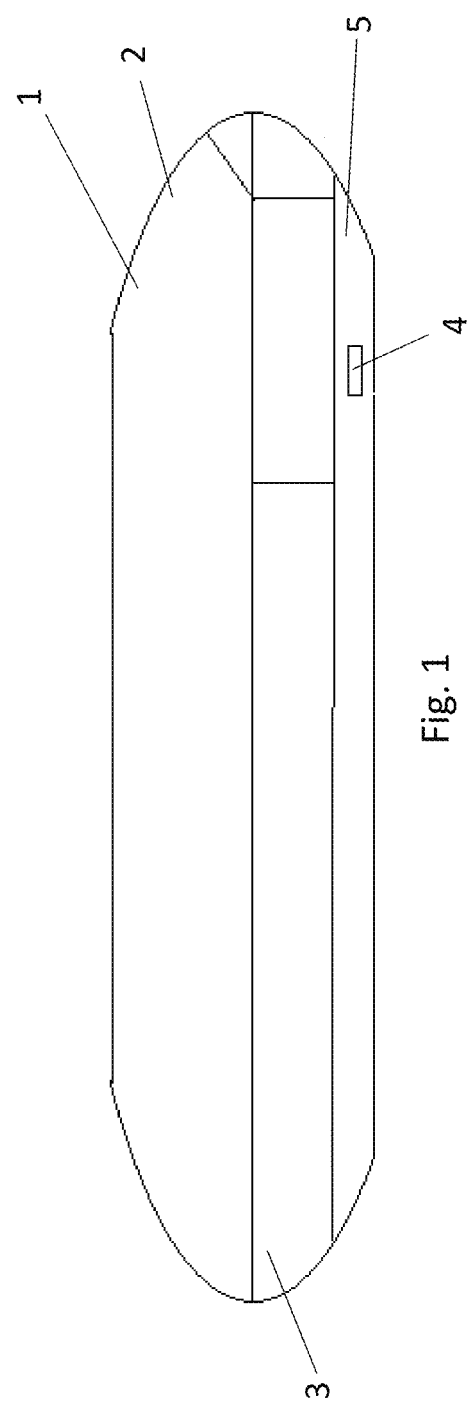
FIG. 1 shows an example of a closed storage device

FIG. 1 shows an exemplified embodiment of a storage device 1 according to the present invention. The storage device comprises a lid 2 and a bottom part 3. The lid 2 can either be attached to a part of the bottom part 3, for example by the use of one or more hinges, or be detachable from the bottom part 3.

The outside of the bottom part 3 of the storage device 1 can further provided with a first means for charging 4 in the form of an outer charging port to charge an electronic device, such as a mobile phone. The first means for charging 4 can for example be a USB-port or any other suitable port for charging mobile phones or other electronical devices. The bottom part 3 further comprises a battery 5.

The person skilled in the art understands that the storage device can have any shape and size as long as the technical features are present. The storage device 1 according to the present invention is preferably of pocket size and can be carried and stored in for example the pocket of a jacket or in a bag.

Figure 2:
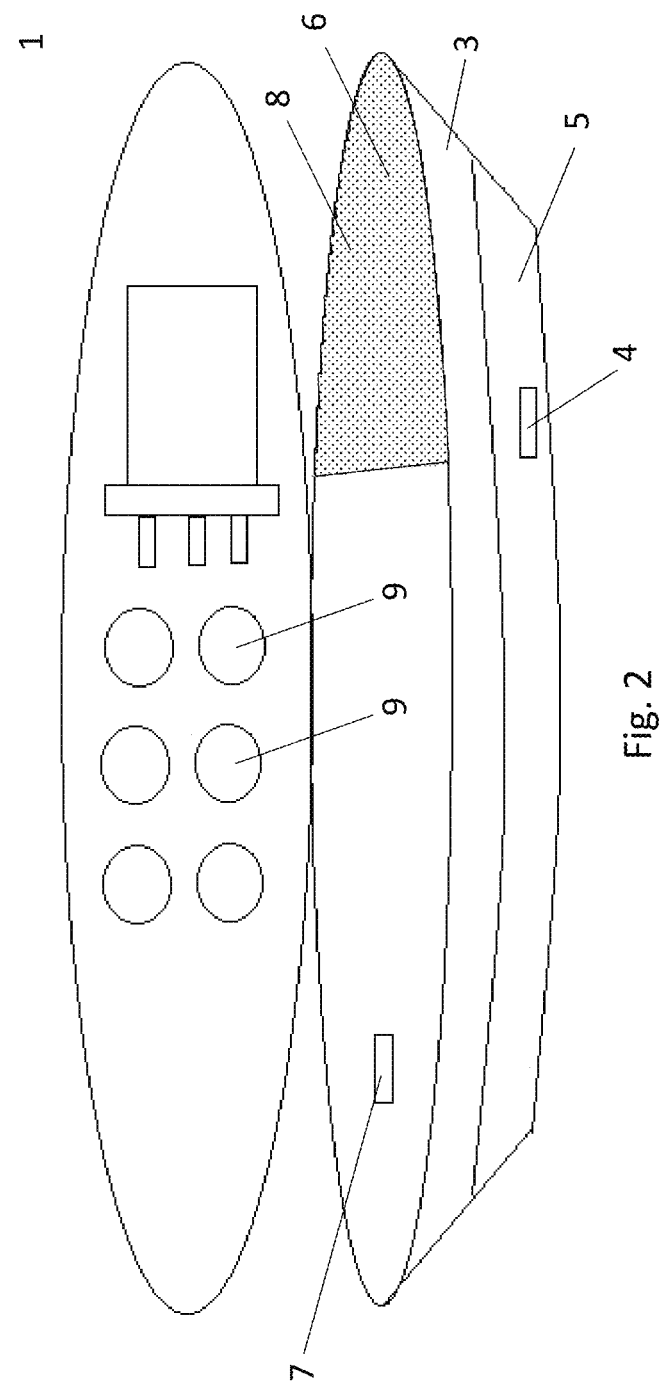
FIG. 2 shows an example of an open storage device

FIG. 2 shows an exemplified embodiment of the inside of a storage device 1 according to the present invention. The inside of the lid 2 of the storage device 1 can for example be provided with different accessories, such as extra earbuds 9, charging accessories etc.

The bottom part 3 of the storage device 1 comprises a compartment 6 for non liquid means for cleaning the headphones. Non-liquid means can for example be an electromagnetic radiator 8 that produces radiation, such as UV-light, IR light, X-rays or gamma rays or a combination of any of these. It could also be a sterilizing gas.

UV-light can be divided into four different types, UV-A, UB-B, UV-C and UV-V, depending on the wavelength. The UV-light used for disinfection is UV-C, with UV-light having a wavelength of 200-280 nm. Short-wave UV-C radiation has an intensive bactericidal effect and can be used to kill or inactivate microorganisms by destroying nucleic acids and disrupting their DNA, leaving them unable to perform vital cellular functions. The treatment takes only a few seconds.

The compartment 6 for UV-cleaning in the bottom part 3 of the storage device can be of different sizes. It can for example constitute only a part of the inner bottom part, as shown in FIG. 2, it can be a smaller part or a larger part or even the entire bottom part.

The storage device 1 can further be provided with a second means for charging 7 in the form of an inner charging port, where for example the headphones can be charged. The second means for charging 7 can for example be a USB-port or any other suitable port for charging headphones, mobile phones or other electronical devices.

The first means for charging 4 is also used to charge the battery 5 of the storage device 1. The battery 5 can be charged with any appropriate charger, for example a USB-charger. The battery 5 is used to run the cleaning and can also be used as a power bank to charge other electronical devices.

The storage device can further be adapted to include different modules such as one or more charging ports for charging the device itself to be able to perform the electromagnetic radiation, as well as further means for charging headphones and/or a mobile phone.

The headphones can be charged in different ways, either by connecting a cord (not shown) from the headphones to a charging port 4,7 inside or outside of the storage device 1. When a cable is used for charging, the charging will begin once the cable has been connected and continue either until the cable is detached or until the headphones are fully charged.

Another possible way charge to the headphones as well as the storage device itself is through NFC (Near-field communication), which is a set of communication protocols that enable two electronic devices, one of which is usually a portable device such as a smartphone, to establish communication by bringing them within a pre-determined distance from each other. The charging of the headphones can either start automatically when the distance between the headphones and the battery is within the pre-determined distance or by an active action. Such an active action can for example be that an indicator, contact or the like are triggered when the headphones are placed inside the storage device.

Yet another possible way to charge the headphones is by wireless charging between the storage device 1 and the headphones, whereby transmission of small amounts of energy takes place wireless from the storage device 1 to the headphones. By using this technique, it will be possible to charge the headphones during use. The storage device can be placed in a pocket or a bag and wirelessly charge the headphones.

When the user is to use the storage device for cleaning the headphones, the headphones are placed inside the storage device 1 in the compartment 6 for UV-cleaning of headphones.

The lid 2 is then closed and the cleaning can be started. The cleaning can either be triggered by the closing of the lid 2 of the storage device 1 or by an on/off-button. When the cleaning is finished, the user can either take out the headphones and use them, or keep them in the storage device 1 until they are fully charged or until the user wants to use them again.

In a further embodiment according to the present invention is described a cleaning device for headphones, which cleaning device comprises an outer shell for the headphones and a means for electromagnetic radiation for the cleaning of the headphones. The cleaning device can be used for storing and cleaning of headphones. The cleaning of the headphones is performed in a similar manner as has been described related to the storage device above.

The cleaning of the headphones using electromagnetic radiation can only be performed once the lid has been closed. It is not possible to start the cleaning process if the lid is not properly closed.

In one embodiment of the present storage device or cleaning device, the cleaning is started automatically when the lid of the device is closed and automatically turned off after a pre-determined time.

The cleaning and the charging can either be done simultaneously or subsequently. In one version, the cleaning is started by closing the lid of the storage device and the charging will start when the cleaning is finished. In another embodiment, the charging is started automatically, as described above, and the cleaning is started by the use of an on/off-button.

It is also possible to use both the cleaning device and the storage device for only storing the headphones, without starting the cleaning or the charging.

The storage device or cleaning device according to the present invention can further be provided with a lining on the inside to enhance the cleaning effect of the UV-light. Such a lining can for example be an aluminum foil or film.

Headphones are also known as ear speakers, earbuds 9, in-ear headphones and earphones.

The invention claimed is:

1. A storage device for earbuds, comprising:
a clam-shell case in which the earbuds are stored and the case forms an internal compartment;
a battery retained by the case;
an inner charger that charges the earbuds with power from the battery; and
an electromagnetic radiator retained within the compartment and that is controlled to emit electromagnetic radiation to clean the earbuds with power from the battery; and
wherein the storage device is portable and sized for carrying in a pocket of clothing of an individual.

2. The storage device for earbuds according to claim 1, wherein the electromagnetic radiation is UV-light, IR light, X-rays, gamma rays or a combination thereof.

3. The storage device for earbuds according to claim 2, wherein the electromagnetic radiation is UV-C light.

4. The storage device for earbuds according to claim 1, further comprising an outer charger port accessible on an outer surface of the case.

5. The storage device for earbuds according to claim 4, wherein the outer charger port is a USB-port.

* * * * *